United States Patent [19]
Muzslay

[11] Patent Number: 5,871,375
[45] Date of Patent: Feb. 16, 1999

[54] HIGH TEMPERATURE SENSOR ASSEMBLY

[75] Inventor: Steven Zoltan Muzslay, Huntington Beach, Calif.

[73] Assignee: ITT Manufacturing Enterprises, Inc., Wilmington, Del.

[21] Appl. No.: 731,318

[22] Filed: Oct. 15, 1996

[51] Int. Cl.⁶ .................................................. H01R 13/40
[52] U.S. Cl. ............................................ 439/599; 439/825
[58] Field of Search .................................. 439/597–600, 439/603, 628, 630, 632, 640, 655, 721, 723, 724, 405, 418, 825

[56] References Cited

U.S. PATENT DOCUMENTS

| | | |
|---|---|---|
| 3,178,673 | 4/1965 | Krehbiel . |
| 3,281,757 | 10/1966 | Bonhomme . |
| 3,315,214 | 4/1967 | Davis . |
| 3,783,440 | 1/1974 | Karube et al. ........................... 439/748 |
| 3,793,610 | 2/1974 | Brishka . |
| 3,957,337 | 5/1976 | Damiano . |
| 4,123,131 | 10/1978 | Pearce . |
| 4,124,264 | 11/1978 | Kato et al. ........................... 439/752.5 |
| 4,193,289 | 3/1980 | Springer et al. ........................... 73/27 |
| 4,206,173 | 6/1980 | Yamaguchi et al. ....................... 422/98 |
| 4,214,472 | 7/1980 | Maxwell et al. ............................. 73/23 |
| 4,222,026 | 9/1980 | Heiney, III et al. ....................... 338/34 |
| 4,223,293 | 9/1980 | Springer et al. ........................... 338/34 |
| 4,225,559 | 9/1980 | Achari et al. ............................. 422/98 |
| 4,228,128 | 10/1980 | Esper et al. ............................... 422/98 |
| 4,228,675 | 10/1980 | Heiney, III et al. ........................ 73/23 |
| 4,237,722 | 12/1980 | Achari ......................................... 73/23 |
| 4,306,444 | 12/1981 | Hattori et al. ............................... 73/23 |
| 4,309,897 | 1/1982 | Springer et al. ............................. 73/23 |
| 4,344,317 | 8/1982 | Hattori et al. ............................... 73/23 |
| 4,420,210 | 12/1983 | Karol . |
| 4,426,124 | 1/1984 | Vandevier . |
| 4,647,132 | 3/1987 | Mikola . |
| 4,668,375 | 5/1987 | Kato . |
| 4,820,199 | 4/1989 | Muzslay . |
| 4,824,550 | 4/1989 | Ker . |
| 4,836,801 | 6/1989 | Ramirez . |
| 4,923,587 | 5/1990 | Nishio et al. ............................ 204/424 |
| 4,940,416 | 7/1990 | Wagaman . |
| 4,983,271 | 1/1991 | Kato . |
| 5,021,001 | 6/1991 | Ramirez . |
| 5,046,964 | 9/1991 | Welsh . |
| 5,120,233 | 6/1992 | Mikola . |
| 5,120,239 | 6/1992 | Witek . |
| 5,288,242 | 2/1994 | Muzslay . |
| 5,329,806 | 7/1994 | McClanahan et al. ................. 73/31.05 |
| 5,490,412 | 2/1996 | Duce et al. ............................ 73/23.31 |

Primary Examiner—Hien Vu
Attorney, Agent, or Firm—Thomas L. Peterson

[57] ABSTRACT

A sensor assembly (10) for measuring oxygen in vehicle exhaust gasses, which must be connected by a plurality of wires (20) to a microprocessor, is modified to facilitate its installation and removal. In the modified assembly, each of a plurality of high temperature metal strips (34), which were previously crimped to cable wires, are instead bent to form contact pin parts (70) that are inserted into passages (74) of an insulative connector insert (72) to form a connector with pin contacts. Portions (120) of the metal strips are bent to have V-shaped cross-sections, to stiffen them against column collapse as the connector insert is moved forwardly to receive the pin parts, with front portions (110) of the insert passages being tapered to facilitate passage of the pin parts.

5 Claims, 4 Drawing Sheets

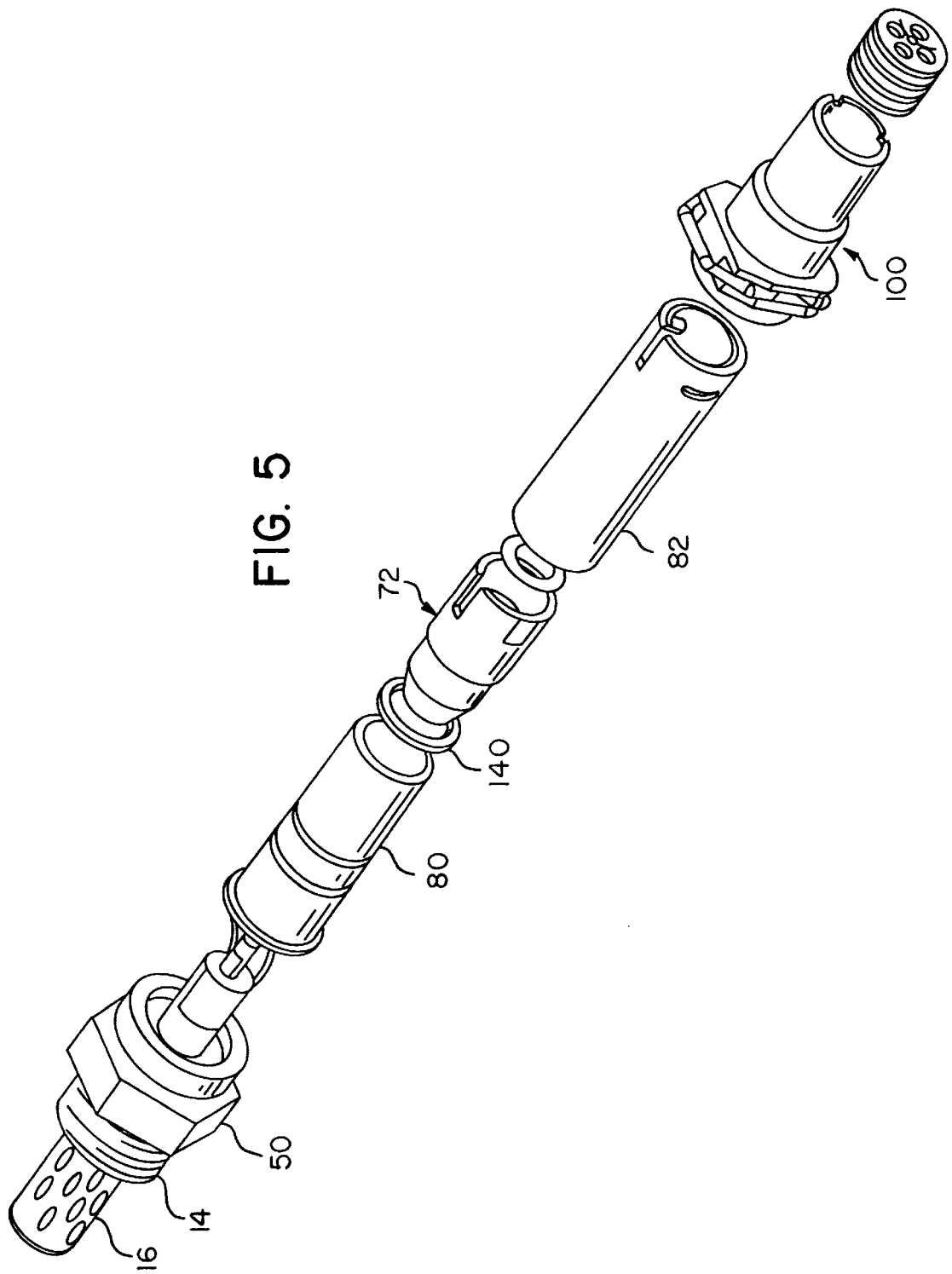

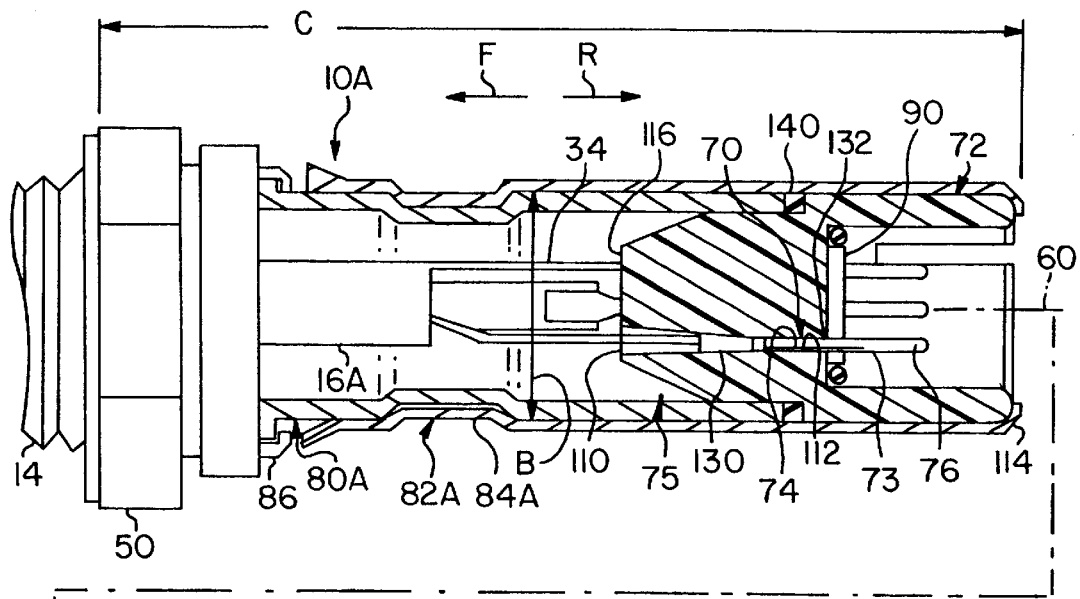
FIG. 6
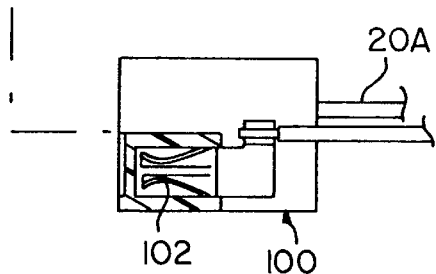
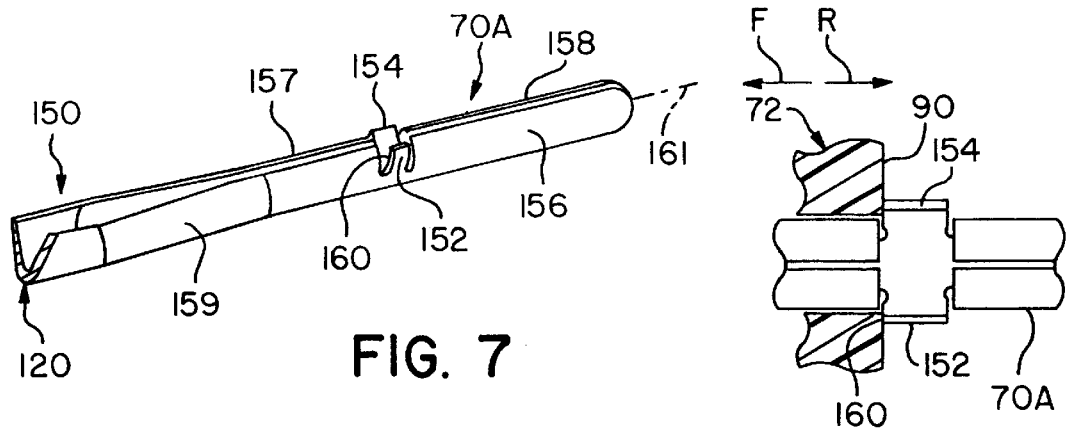
FIG. 7
FIG. 8

HIGH TEMPERATURE SENSOR ASSEMBLY

BACKGROUND OF THE INVENTION

Oxygen sensor assemblies that detect the concentration of oxygen in engine exhaust gasses, are widely used to control the air/fuel ratios in vehicles. Each sensor assembly includes a metal housing with a threaded shank that screws into a threaded opening in the exhaust pipe and a perforated tube that projects into the exhaust pipe to receive exhaust gasses so they can pass by an oxygen sensor device. A plurality of electrically conductive strips of a high temperature material such as Inconel extend from the sensor device. Rear ends of the strip conductors are crimped to wires that extend through a spacer that controls their positions, with the wires extending to a microprocessor in the vehicle. The long lengths of wires extending from the exhaust sensor assembly makes it more difficult to install the sensor assembly. It is usually desirable to turn the parts by a power driven socket wrench of several inches length that extends around the entire sensor assembly and that engages a wide nut near the front end of the assembly. The long wires prevent the use of some of such socket wrenches. The long wires also make it more difficult to use socket wrenches because the long wires may whip around as the sensor assembly is turned to thread it into place. Also, if the sensor assembly must be replaced, then the set of wires also must be replaced, which adds to the cost. A high temperature vehicle exhaust sensor assembly which facilitated installation and replacement, would be of value.

SUMMARY OF THE INVENTION

In accordance with one embodiment of the present invention, a high temperature vehicle exhaust sensor assembly is provided that is minimally changed from prior proven sensor assemblies, but which facilitates installation and replacement of the sensor assembly. The present sensor assembly includes a sensor device mounted on a front portion of the housing and a plurality of electrically conductive metal strips connected to the sensor device and extending rearwardly therefrom. Instead of forming rear ends of the conductive strips so they crimp to wires, the rear ends are bent to a largely cylindrical shape to form a pin part. The separator that normally separates the wires, is replaced by a connector insert that closely positions the pin parts to form a connector with pin contacts that can mate with socket contacts of a mating second connector. The mating second connector connects to wires that extend to the vehicle microprocessor, so the sensor assembly is of only moderate length and does not include long wires.

The connector insert which has a plurality of through passages, can be formed so the front portion of each through passage is tapered in width. The tapered passage portion can readily receive the pin parts as the insert is moved forwardly into a blind hole region at the rear of the sensor assembly. Also, portions of the metal conductive strips are bent to a V-shape to stiffen them against collapse to help the pin parts to enter the passages. Each of the pin parts can be formed with a pair of latch bits that snap against a rear surface of the connector to lock the pin part therein so it does not move forwardly when mating with a socket contact of a second connector.

The novel features of the invention are set forth with particularity in the appended claims. The invention will be best understood from the following description when read in conjunction with the accompanying drawings.

BRIEF DESCRIPTION OF THE DRAWINGS

FIG. 5 is an exploded isometric view of a sensor assembly which includes the portions shown in FIG. 3, and also showing a mating connector device.

FIG. 6 is a sectional side view of the sensor assembly of FIG. 3 including the metal pipe and shell thereof, showing the parts assembled and including a simplified view of a mating second connector.

FIG. 7 is an enlarged partial isometric view of a pin part that is modified in accordance with a second embodiment of the invention to have latch bits.

FIG. 8 is a partial sectional view of a connector with the pin part of FIG. 7 installed therein.

DESCRIPTION OF THE PREFERRED EMBODIMENTS

Figure 1:
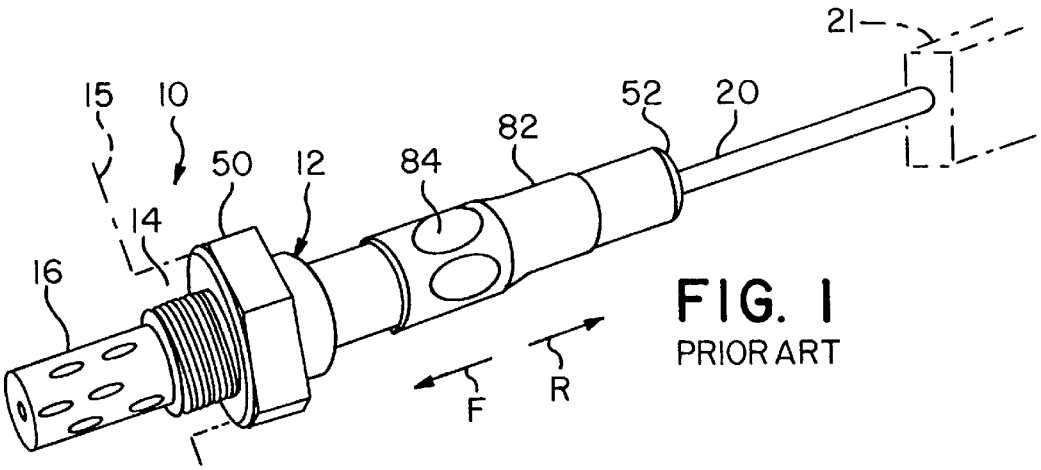
FIG. 1 is a rear and side isometric view of a sensor assembly of the prior art, showing only a portion of the wires thereof.

FIG. 1 illustrates a prior art vehicle exhaust sensor assembly 10 which includes a housing 12 having a threaded shank 14. The threaded shank is generally screwed into a threaded port leading to a vehicle exhaust pipe 15 so a sensor device 16 of the assembly is exposed to the exhaust gasses. The sensor device generates signals indicating the amount of oxygen in the exhaust gasses, with the signals being passed along wires 20 that extend to a control 21 in the vehicle. The control may include a microprocessor that passes currents through the wires and measures the partial pressure of oxygen by the resistance of the sensor device. The microprocessor uses the data to control the fuel-to-air ratio applied to the engine to reduce pollution, and increase mileage.

Figure 2:
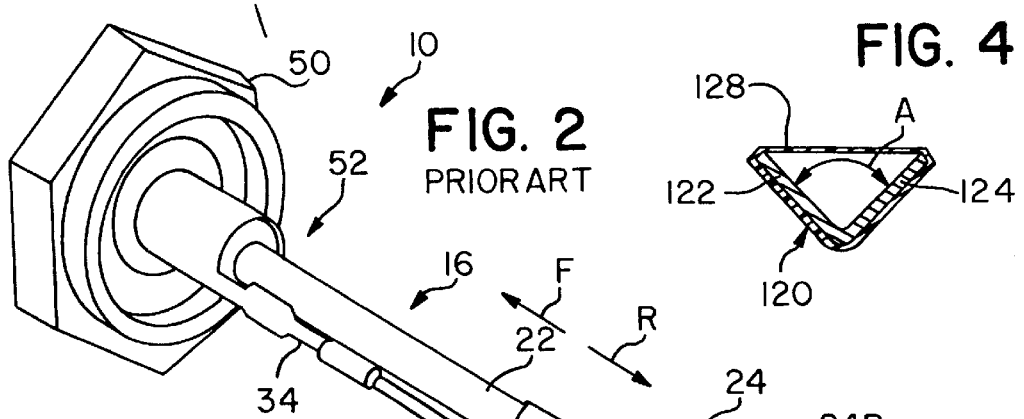
FIG. 2 is a front and side isometric view of the prior art sensor assembly of FIG. 1, with the metal pipe and shell removed, and with the spacer shown in phantom lines.

As shown in FIG. 2, the sensor device 16 includes a dielectric rod 22 and a plurality of conductive metal strips 24 extending rearwardly thereof. There are four strips 24A, 24B, 24C, 24D, that carry electrical signals representing the amount of oxygen in the exhaust gasses. The conductive strips are formed of a high temperature metal such as Inconel or stainless steel. Rearward end portions of the strips are connected to the wires by forming the rear ends of the strips at 40 so they can encircle insulation-stripped ends of the wires and can be crimped to the stripped ends. The wires 20 pass through holes 42 in an insulator 44 which controls their positions before they pass as a harness to the vehicle engine control. It is noted that high temperature shrink wrap tubing may be placed around the strips to electrically insulate them.

The sensor assembly 10 is installed by applying a wrench to a hexagonal nut 50 of the housing. The length of the sensor assembly between the nut 50 and its rear end 52 (FIG. 1) is only about three inches, so the nut could be turned by a socket wrench of about three one-half inches length for rapid and torque-controlled power tool installation.

However, the long lengths of wires 20 projecting from the rear of the sensor assembly makes rapid installation difficult. It is difficult to mount a socket wrench around the nut for installation, and the wires 20 could be harmed if the sensor assembly 10 is rapidly rotated during installation. Also, replacement of a sensor assembly previously required replacement of the wires 20, which added expense especially if the far ends of the wires 20 were crimped or soldered to contacts at the control. It would be desirable if a vehicle sensor were available that could be readily installed and replaced. However, it is highly desirable to retain most of the construction of the prior art sensor assembly, especially the front portion 52 where the sensor device 16 is mounted and lies, to minimize the redesign. It may be noted that the sensor assembly 16 may be exposed to exhaust gasses and temperatures of several hundred degrees centigrade.

Figure 3:
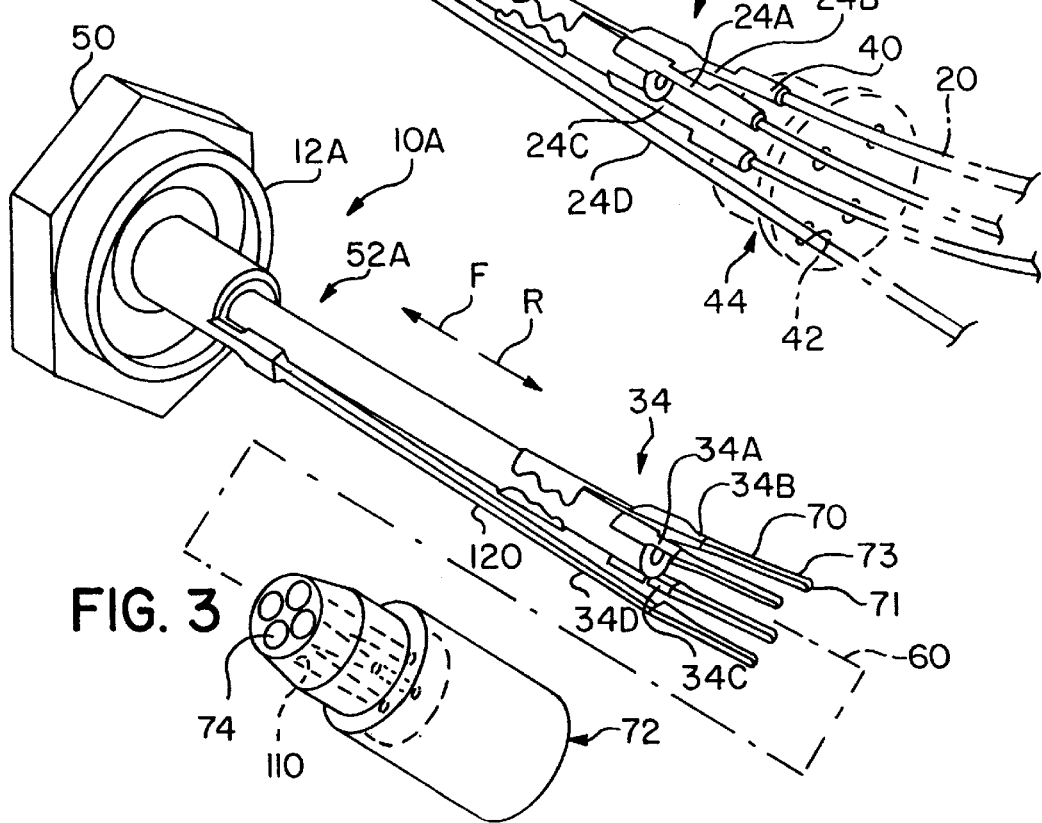
FIG. 3 is a front and side isometric view of a present sensor assembly, taken from a position similar to that of FIG. 2, and with the metal pipe and shell removed, where the sensor assembly is modified in accordance with the present invention, and where the insert is shown in a rear isometric view.

FIG. 3 illustrates a portion of a sensor assembly 10A of the present invention, whose front portion 52A is preferably identical to the front portion 52 of the prior art sensor assembly. It includes a housing 12A extending along a housing axis 60. One modification is that the electrically conductive strips 34, labelled as 34A–34D are constructed with their rear portions bent to form sleeve-shaped pin parts 70 with largely cylindrical rearward pin part portions 73 having rounded extreme rear ends 71. In addition, instead of a spacer, a receptacle connector insert 72 is provided which has through passages 74 through which the pin parts 70 project. The combination of pin parts 70 and insert 72 form a connector, or electrical connector portion 75 that is integral with the sensor assembly 10A.

FIG. 6 shows the construction of the present sensor assembly 10A. Most of the parts are the same as those of the prior art assembly of FIGS. 1 and 2, including the sensor device 16A, threaded shank 14, nut 50, metal pipe 80A of the housing, and shell 82A (although the metal pipe and shell 80, 82 may be modified at their rear ends). As in the prior art, a crimp location 84A is provided where the shell 82A is crimped around the pipe 80A to hold them together, and with a short cylinder 86 extending rearwardly from the nut 50 and crimped around a flange at the front of the pipe. However, the conductive strips such as 34 are made longer by the original sensor assembly manufacturer, and the strip rear ends are bent to form the pin parts 70. It can be seen that the connector insert 72 has an insert rear surface 90 at the rear of the passages 74, and the pin part rear portions 73 have rear contact locations or sections 76 that project rearwardly of the surface 90. A mating second connector shown in simplified view at 100, has socket contacts 102 that can mate with the rear contact sections 76 of the pin parts. Wires 20A extend from the mating connector and can connect to a vehicle control.

Thus, each conductive strip 34 has a forward section 132 mounted in a passage 74 of the insert and has a rear section 76 projecting forward of the passage. The rear sections 76 of the conductive strips 34 are shaped and positioned to mate with the electrical contacts 102 of the second connector 100 upon interengagement of the electrical connector portion 75 with the second connector. The rear sections 76 of the conductive strips therefore form mateable contact parts 76 that can mate with contacts 102 of the second connector when the connector portion 75 is mated to the second connector 100. The particular conductive strip rear sections, or mateable contact parts, that are illustrated, comprise sheet metal bent into a cylinder.

It can be seen that each passage 74 of the connector insert 72 has a tapered forward portion 110 and a constant width rearward portion 112. This construction is used because the connector insert 72 is installed by moving it forwardly in the direction of arrow F into the rear end of the metal pipe 80A. The electrically conductive strips such as 34, whose rearward ends have been bent to form pin parts, are positioned to be in line with the passages 74 in the insert. The tapered forward portions 110 of the passages help reception of the pin parts in the passages as the insert 72 is moved forwardly. Once rear contact sections 76 of the pin parts 70 have moved rearward of the insert rear surface 90, they can be grasped with a tool and pulled rearwardly to their final fully inserted positions in the insert. It is noted that for most prior art electrical connectors, contacts can be grasped and pushed through passages in the connector insert. In the present case, because the forward end 116 of the insert is not accessible during assembly, this cannot be readily accomplished.

Figure 4:
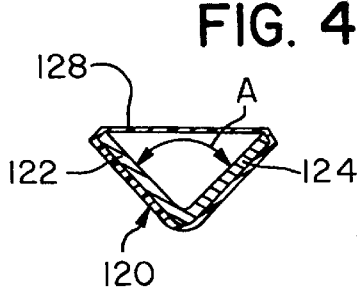
FIG. 4 is a sectional view of a forward portion of one of the metal strips of the sensor assembly of FIG. 3.

To stiffen the electrically conductive strips, applicant bends portions 120 of them as shown in FIG. 4, to largely V-shaped cross-sections. That is, the sections 120 have opposite sides 122, 124 that extend at an angle A that is preferably about 90°, that is, between 45° and 135°, so they have stiffness against column-like collapse. A high temperature shrink tube 126 that is shrunk around the contact portion, not only electrically insulates it from the other strip conductors, but increases the rigidity against column-like collapse, in part because a portion 128 of the shrunk tube forms a third side of a triangle.

Referring again to FIG. 6, it can be seen that the pin part 70 can be formed with a tapered front portion 130. When the projecting rearward pin part portion 73 is pulled forwardly, the tapered front pin part portion 130 or the forward section 132 of portion 73 can be jammed into the passage 74, which prevents rearward or forward movement of the contacts formed by the pin parts 70 during mating and unmating to the second connector device 100. The forward section 132 of portion 73 lies in a cylindrical part of the passage to help fix the orientation of the pin part. It may be noted that applicant prefers to provide a flat O-ring at 140 to seal the space between the inside of the shell 82A and the pipe 80A and the insert 72. After the insert is fully installed, the rear end of the shell can be rolled over as shown at 114, and the rolled-over end can be used to push the insert forwardly to compress the O-ring 140. However, applicant prefers to roll over the rear end 114 when the shell is originally formed, to then push the shell forwardly into position, and to then crimp the shell around the pipe 80A at crimp location 84A.

FIG. 7 shows a modified pin part 70A of a conductive strip 150, which is similar to that of FIGS. 1–6, except that the pin part is formed with a pair of latch bits 152, 154. As in the case of the pin part of FIG. 6, the sheet metal strip has been bent to form a sleeve-shape with a cylindrical outer surface 156 having front and rear sections 157, 158, and with a taper at 159. A forward portion of the strip is bent to a V-shape at 120. Applicant forms the opposite sides of the pin portion 70A with slits that leave the latch bits 152, 154. The latch bits extend partially radially (with respect to the pin part axis 161) beyond the cylindrical surface 156.

The latch bits 162, 154 are in the form of resiliently bendable tines. FIG. 8 shows that when the pin part 70A is pulled completely rearwardly to its final position, the latch bits 152, 154 are initially resiliently deflected or compressed to a cylindrical shape, but then spring out when they pass rearwardly of the insert rear surface 90. The latch bits have forward shoulders 160 that substantially abut the insert rear surface 90 to prevent the pin part 70A from moving forwardly (F) during mating. It may be noted that in FIG. 7, the tapered front portion 159 of the strip pin part forms an abutment, as shown for tapered front portion 130 in FIG. 6, which abuts the tapered forward front portion 110 of the passage to prevent the contact from moving rearwardly any further than a position wherein the abutment 130 presses firmly against the tapered passage walls.

Figure 9:
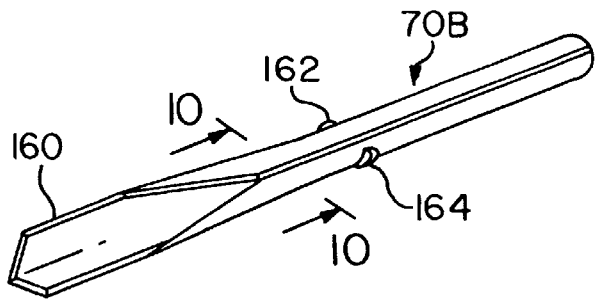
FIG. 9 is a partial isometric view of a pin part that is modified in accordance with a third embodiment of the invention to have latch bits.
Figure 10:
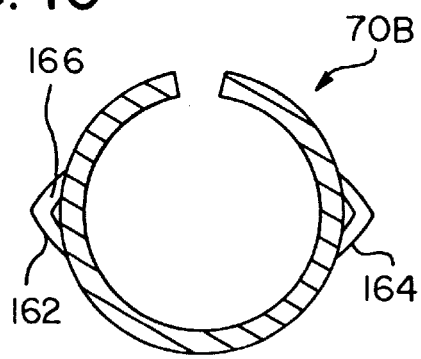
FIG. 10 is a view taken on line 10—10 of FIG. 9.
Figure 11:
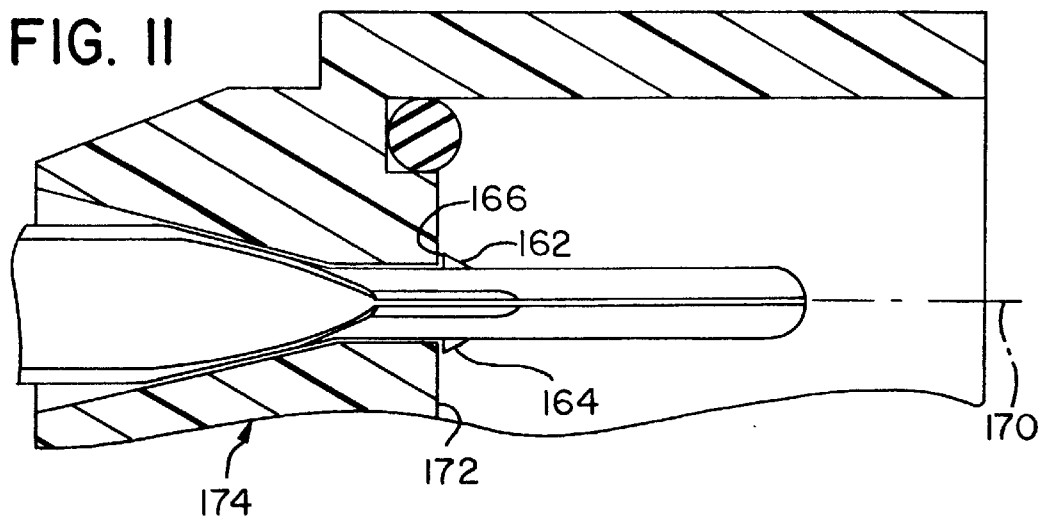
FIG. 11 is a partial sectional view of a connector with the pin part of FIGS. 9 and 10 installed thereon.

FIGS. 9–11 show another modified pin part 70B of a conductive strip 160, with a pair of latch bits 162, 164. In this case, the latch bits are coined in the strip, before the strip is bent into the shape of the pin part. As the pin part moves rearwardly with respect to the insert 174, during installation, opposite sides 168, 169 of the pin part near the latch bits, are deflected together as indicated in phantom lines in FIG. 10. The gap 176 formed by the bent strip, is provided with sufficient width E at the gap location 176A of the latch bits to allow the walls of the gap to move together. The wider gap location 176A is provided because the latch bits 162, 164 are substantially rigid (the sides 168, 169 deflect more than the latch bits during installation). The gap 176 preferably extends at least 10° about the pin part axis to enable substantial latch bit movement toward the axis. At the end of pin part installation, shoulders 166 (FIG. 11) on the latch bits snap radially outward with respect to the pin axis 170, to lie immediately rearward of a rear wall 172 of the connector insert 174. It is possible to also coin a forward portion of the pin part to engage a forwardly-facing surface on the insert to limit rearward (R) movement of the pin part. It also is possible to form a contact by crimping a rear end of a strip to a separate pin, although this is generally not preferred.

Applicant has designed sensor assemblies of the constructions shown in the figures, which each assembly has a diameter B (FIG. 6) of 18.5 millimeters and a length C of about three inches (to the front end of the nut). The assembly can be installed by a socket wrench whose front end is a hexagon and that closely surrounds the nut 50, and which extends slightly more than three inches rearward of its front end so it can be mounted on a power wrench that rapidly turns the nut to install or remove the assembly from a threaded port in a vehicle exhaust pipe. The fact that the socket can be readily applied to the nut, and that the sensor assembly can be rapidly rotated without harm to long extending wires, makes assembly and removal easy.

All parts of the sensor assembly (e.g. 10A of FIG. 6) are constructed of material that can function in a high temperature environment. This is because the front end of the assembly is in contact with exhaust gasses that may be of a temperature such as 600° C. The temperature of the assembly rapidly decreases at more rearward locations, so a maximum temperature such as 250° C. may exist at the connector insert 42 which can be made of a high temperature engineering plastic. There is a further drop in temperature across the interface where the second connector 100 connects to the sensor assembly, so that lower temperature construction can be used at the second connector 100.

Thus, the invention provides a high temperature vehicle exhaust sensor assembly, especially one for measuring oxygen in exhaust gasses, which is only moderately modified from a prior art widely-accepted sensor assembly, and which can be readily installed and removed. The conductors extending from the sensor device, which are generally of strip shape, are made somewhat longer, and with their rear portions bent to form sleeve-shaped pin parts. Instead of using a spacer with holes through which wires extend, a dielectric connector insert is installed, which has passages through with the pin parts are projected, so rear contact sections of the pin parts project beyond an insert rear surface to provide pin contacts for mating with a second connector device. Installation of the connector insert usually requires that the insert be moved blindly forwardly as the stationary pin parts at the rear of the conductive strips are received in the passages. The conductive strips are rigidized by bending them into V-shapes. The passages preferably have tapered front portions to help guide the pin parts into and along the passages. The pin parts can be formed with latch bits to lock them in place.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A high temperature vehicle exhaust sensor assembly that includes a housing having a housing axis extending in forward and rearward directions, a sensor device mounted on a front portion of said housing, and a plurality of electrically conductive strips having forward portions coupled to said sensor device and extending rearwardly therefrom, including:

a connector insert of high temperature insulative material, said insert having a plurality of generally axially-extending through passages, said insert being mounted in said housing; and wherein each of said conductive strips includes said forward portion, a middle portion and a rearward portion, with said rearward portion forming a pin, said middle portion being bent about a corresponding pin axis that extends substantially parallel to said housing axis with each of said pins having a forward section lying in one of said passages so the insert and the pins therein form a connector;

each of said insert passages has a front passage portion of tapered width to have a smaller cross-section at progressively more rearward locations therealong, and each of said insert passages has a rearward passage portion of substantially cylindrical shape and which closely surrounds a corresponding one of said pins.

2. The assembly described in claim 1 wherein:

each of said conductive strips has a forward region that lies forward of said contact part and that is bent so its cross-section is generally V-shaped with opposite sides extending at an angle of between 45° and 135°.

3. The assembly described in claim 1 wherein:

said housing includes a threaded shank, a metal pipe surrounding said housing axis and extending rearwardly from said shank and surrounding said strip forward portions and having a pipe rear end, and said housing includes a shell that extends around and rearward of said pipe with said shell having a forward portion crimped to said pipe and having a rearward portion extending rearward of said pipe rear end;

said insert has an outside surface with a front portion that lies closely within said pipe and a rear portion that is of larger outside diameter than said front portion and that lies rearward of said pipe rear end and closely within said shell rearward portion, said insert outside surface forming a forwardly-facing shoulder at the intersection of said outside surface front and rear portions, and said insert outside surface forward portion having a front end;

an O-ring that lies between said pipe rear end and said shoulder;

said shell having a rear end that Is bent radially inwardly and that abuts said insert front end and that presses said Insert forwardly to compress said O-ring.

4. A high temperature vehicle exhaust sensor assembly that includes a housing having a housing axis extending in forward and rearward directions, a sensor device mounted on a front portion of said housing, and a plurality of electrical conductors connected to said sensor device and extending rearwardly therefrom, including:

an insulative connector insert having a plurality of through passages, said insert mounted in said housing;

each of said conductors has a rear end fixed to said connector insert, and each conductor rear end forms a pin part with a cylindrical portion having a rear section constructed to mate with a socket contact;

a second connector device which has a plurality of socket contacts that are mateable to said pin part rear sections and a plurality of wires each connected to one of said socket contacts;

said insert passages each including a forward passage portion that is tapered in a width dimension that is perpendicular to said housing axis, to have a progressively smaller width at progressively more rearward locations, and each including a rearward passage portion of constant width to closely surround a forward section of said cylindrical portion of one of said pin parts.

5. The sensor assembly described in claim 4 wherein:

said insert has a largely rearwardly-facing rear wall portion at the rear end of each passage;

each of said pin parts has a pin part axis and has a pair of circumferentially spaced latch bits which are constructed to be resiliently deflected radially inwardly toward the corresponding pin part axis as the pin part is moved rearwardly through one of said passages, with each pin part forming a forwardly-facing shoulder to snap behind the rear wall portion and prevent forward movement of the pin part.

* * * * *